United States Patent
Bell et al.

[11] Patent Number: 6,153,292
[45] Date of Patent: Nov. 28, 2000

[54] BIOPOLYMER FOAMS FOR USE IN TISSUE REPAIR AND RECONSTRUCTION

[75] Inventors: Eugene Bell, Boston; Tracy M. Sioussat, Reading; Timothy W. Fofonoff, Dedham, all of Mass.

[73] Assignee: Tissue Engineering, Inc., Boston, Mass.

[21] Appl. No.: 09/282,088

[22] Filed: Mar. 30, 1999

Related U.S. Application Data

[62] Division of application No. 08/754,818, Nov. 21, 1996, Pat. No. 5,891,558, which is a continuation of application No. 08/343,172, Nov. 22, 1994, Pat. No. 5,709,934.

[51] Int. Cl.[7] .................................. A61F 2/06; B32B 3/26
[52] U.S. Cl. ..................................... 428/305.5; 428/315.7; 428/317.9; 428/321.7; 442/30; 442/221; 442/370; 623/1; 623/13; 623/15
[58] Field of Search .............................. 442/370, 30, 221; 428/318.4, 323, 305.5, 317.9, 315.7, 321.7; 623/1, 13, 15

[56] References Cited

U.S. PATENT DOCUMENTS 3,800,792  4/1974  McKnight et al. ..................... 128/156
4,553,272  11/1985  Mears ......................................... 623/1

FOREIGN PATENT DOCUMENTS

85/04413  10/1985  WIPO ............................. C08L 89/06

*Primary Examiner*—Blaine Copenheaver
*Attorney, Agent, or Firm*—Lahive & Cockfield, LLP

[57] ABSTRACT

Single and double density biopolymer foams, composite biopolymer foams including both single and double density foams, and methods of preparing these foams and composite foams are described. Also described are biocompatible constructs which include single or double density biopolymer foams and extracellular matrix particulates and methods of preparing these constructs. The foams, composite foams, and biocompatible constructs of the invention can be used in tissue repair and reconstruction.

22 Claims, No Drawings

BIOPOLYMER FOAMS FOR USE IN TISSUE REPAIR AND RECONSTRUCTION

This application is a divisional application of Ser. No. 08/754,818 filed on Nov. 21, 1996, now U.S. Pat. No. 5,891,558, which in turn is a continuation application of Ser. No. 08/343,172 filed on Nov. 22, 1994, now U.S. Pat. No. 5,709,934. The contents of all of the aforementioned application(s) are hereby incorporated by reference.

SUMMARY OF THE INVENTION

Collagen sponges or foams have been used as hemostatic agents and more recently as scaffolds for tissue repair in vivo and as research tools in vitro for seeding various cell types to study cell functions in three dimensions. Collagen sponges have a low immunogenicity and consist of a naturally occurring structural protein to which cells can attach, interact with and degrade. In vivo, these sponges are bioabsorbable. However, sponges are usually crosslinked to provide the degree of wet strength and measured resistance to dissolution needed for many of the above-referenced uses. In general, aldehydic crosslinking of collagen sponges or foams reduces or degrades the normal binding sites to which cells and certain molecules secreted by cells attach. Further, collagen sponges, gelatin sponges or polyvinyl alcohol sponges lack biological activity typically present in the extracellular matrix environment of cells. However, because of their deficiencies, crosslinked collagen sponges induce little regeneration in vivo or serve poorly as histiotypic and organotypic models in vitro.

A need exists, therefore, for an improved biopolymer foam that overcomes or minimizes the above-mentioned problems.

BACKGROUND OF THE INVENTION

The invention features biopolymer foams, composite biopolymer foams, biocompatible constructs comprising biopolymer foams and extracellular matrix particulates and methods for making and using these foams and foam compositions. The foams and foam compositions can be used in vitro, for example, for model systems for research, or in vivo as prostheses or implants to replace damaged or diseased tissues or to provide scaffolds which, when occupied by cells, e.g., host cells, are remodeled to become functional tissues. In either case, the foams and foam compositions can be seeded with cells, e.g., mammalian cells, e.g., human cells, of the same type as those of the tissue which the foams or foam compositions is used to repair or reconstruct. Examples of tissues which can be repaired and/or reconstructed using the foams and foam compositions described herein include nervous tissue, skin, vascular tissue, muscle tissue, connective tissue such as bone, cartilage, tendon, and ligament, kidney tissue, and glandular tissue such as liver tissue and pancreatic tissue. In one embodiment, the foams and foam compositions seeded with tissue specific cells are introduced into a recipient, e.g., a mammal, e.g., a human. Alternatively, the seeded cells which have had an opportunity to organize into a tissue in vitro and to secrete tissue specific biosynthetic products such as extracellular matrix proteins and/or growth factors which bond to the foams and foam compositions are removed prior to introduction of the foams and foam compositions into a recipient.

Accordingly, the invention pertains to single density biopolymer foams having selected characteristics. In a preferred embodiment, the single density biopolymer foams comprise a network of communicating microcompartments having biopolymer molecules and/or biopolymer filaments interspersed within the walls of the microcompartments. The microcompartments of these foams typically have volume dimensions of x, y, and z, wherein x=length, y=width, and z=height, are substantially equal, and range from about 1 $\mu$m to about 300 $\mu$m, preferably from about 50 $\mu$m to about 100 $\mu$m. The average wall thicknesses of the microcompartments of the single density biopolymer foams is less than about 10 $\mu$m. Examples of biopolymers which can be used in the single density biopolymer foams include collagen, alginic acid, polyvinyl alcohol, elastin, chondroitin sulfate, laminin, fibronectin, fibrinogen, and combinations of these biopolymers. A preferred biopolymer is collagen, e.g., porcine fetal collagen. In other embodiments, the single density biopolymer foams can include extracellular matrix particulates and/or cells.

Single density biopolymer foams of the invention can be prepared by forming a biopolymer solution, crosslinking the biopolymer in the biopolymer solution, and freeze-drying the biopolymer solution to form a single density biopolymer foam. In another embodiment, the crosslinking step occurs after the freeze-drying step. In a preferred embodiment, the method also includes a step, prior to the crosslinking step, of polymerizing the biopolymer in the biopolymer solution to form a biopolymer lattice. When collagen, the preferred biopolymer, is used in this method, it can be crosslinked by priming with lysyl oxidase. To reduce splitting of the foam, the biopolymer can also be freeze-dried in the presence of an anti-freeze polypeptide, e.g. a type I, I, or III anti-freeze polypeptide, or an anti-freeze glycoprotein. The invention also pertains to single density biopolymer foams prepared by this method.

The invention also pertains to double density biopolymer foams having selected characteristics. In a preferred embodiment, the double density biopolymer foams comprise a network of communicating microcompartments having biopolymer molecules and/or biopolymer filaments interspersed within the walls of the microcompartments. The microcompartments of these foams typically have volume dimensions of x, y, and z, wherein x=length, y=width, and z=height and two of which are substantially equal and range from about 1 $\mu$m to about 300 $\mu$m and the third of which is less than the two dimensions which are substantially equal. The average wall thicknesses of the microcompartments of the double density biopolymer foams is less than about 10 $\mu$m. Preferred biopolymers for use in double density foams are described herein. In other embodiments, the double density biopolymer foams can include extracellular matrix particulates and/or cells.

Double density biopolymer foams of the invention can be prepared by forming a biopolymer solution and then crosslinking the biopolymer in the biopolymer solution. The biopolymer solution can then be freeze-dried to form a foam, hydrated, and shaped to have a selected form. The foam having the selected form can then be dried to yield the double density biopolymer foam. In another embodiment, the crosslinking step occurs after the freeze-drying step. In a preferred embodiment, the method for preparing double density biopolymer foams includes, prior to the crosslinking step, the step of polymerizing the biopolymer in the biopolymer solution to form a biopolymer lattice. The invention also pertains to double density biopolymer foams prepared by this method.

Composite biopolymer foams which include both single and double density foams are also specifically contemplated by the invention. The foams or composite foams can further be conditioned with cells prior to use in vitro or in vivo.

Composite biopolymer foams are formed by first providing a double density biopolymer foam and then hydrating the double density biopolymer foam with, for example, water or a biopolymer solution. A biopolymer solution is then added to the hydrated double density biopolymer foam and the solution and hydrated double density foam are freeze-dried to form a composite biopolymer foam. Prior to the freeze-drying step, the biopolymer in the biopolymer foam can be crosslinked. The invention also includes composite biopolymer foams prepared by this method. The single density and double density foams of the composite biopolymer foam can also be freeze-dried after cell conditioning.

In another aspect, the invention pertains to biocompatible constructs which include single or double density biopolymer foams and extracellular matrix particulates. The extracellular matrix particulates can be dispersed throughout the foam, e.g., the extracellular matrix particulates are included within in a biopolymer solution or suspension which is dispersed throughout the foam and/or which is coated on the surface of the biopolymer foam. The biopolymer foam with the extracellular matrix particulates can then be freeze-dried.

In yet another aspect, the invention pertains to methods for preparing biopolymer-coated, e.g., collagen-coated, single or double density foams. These methods include preparing the single or double density foams by the methods described herein and then applying a biopolymer solution, which can further include extracellular matrix particulates, to the foams, thereby forming a biopolymer-coated foam. After the foam has been coated, it can be freeze-dried.

The invention also pertains to methods for preparing extracellular matrix particulate-coated single or double density foams. These methods include preparing the single or double density foams by the methods described herein and then applying extracellular matrix particulates, e.g., extracellular matrix particulates suspended in a collagen solution, to the foams, thereby forming an extracellular matrix particulate-coated foam. In one embodiment, the coated foam can then be freeze-dried.

The biopolymer foams and foam compositions, with or without extracellular matrix particulates, of the invention can be used, for example, as skin substitutes or skin dressings, vascular implants, orthopedic implants, dental implants, connective tissue implants, e.g., cartilage implants, urological implants, and glandular implants. Typically, the biopolymer foams and foam compositions are conditioned with cells. In a preferred embodiment, the biopolymer foams and foam compositions can be used as skin dressings. The skin dressing can be a composite biopolymer foam which includes a single density collagen foam and a double density collagen foam. The single density biopolymer foam can be conditioned with human dermal fibroblasts and the double density foam can be conditioned with human keratinocytes such that a stratum corneum is formed. After cell conditioning, the single and double density biopolymer foams of the composite can be freeze-dried. In another embodiment, the skin dressing can be a double density biopolymer foam which has dermal fibroblasts dispersed throughout the foam and epidermal cells on one surface of the foam.

The foams and foam compositions of the invention can also be used as vascular prostheses. In one embodiment, the vascular prosthesis is a double density biopolymer foam or a composite biopolymer foam in the form of a tube. In a preferred embodiment, the tubular vascular prosthesis includes endothelial cells on its luminal surface and smooth muscle cells throughout and on its abluminal surface. The vascular prosthesis can also include a layer of adventitial cells on the smooth muscle cells. After cell conditioning, the double density biopolymer foam or composite biopolymer foam of the vascular prosthesis can be freeze-dried.

Orthopedic and dental implants can also be produced from the foam and foam compositions, with or without extracellular matrix particulates, of the invention. Typically, the foam and foam compositions which are used as orthopedic and dental implants include calcium phosphate cement. An example of such a dental implant is an alveolar ridge builder which is composed of a double density biopolymer foam in the form of a tube containing resorbable calcium phosphate cement. Alternatively, the biopolymer foams and foam compositions can be produced to include hydroxyapatite and used, for example, as dental implants. An alveolar ridge substitute which includes a double density biopolymer foam in the form of a tube containing nonresorbable hydroxyapatite is an example of such a dental implant.

Also contemplated herein are dental implants capable of promoting periodontal ligament repair and bone rebuilding and methods for promoting periodontal ligament repair and bone rebuilding using these implants. Typically, these dental implants include an apron shaped double or quadruple density biopolymer foam. In one embodiment, the apron shaped double or quadruple density biopolymer foam includes an outpocketing containing calcium phosphate cement. To promote periodontal ligament repair and bone rebuilding, an area of tooth requiring periodontal ligament repair and bone rebuilding is contacted with the apron shaped foam, e.g., by the tying the strings of the double or quadruple density biopolymer foam around a tooth to secure the apron to an area of tooth requiring periodontal ligament repair and bone rebuilding.

In yet another aspect, the biopolymer foams and foam compositions of the invention can be used as connective tissue implants, e.g., cartilage, tendon, ligament implants. In one embodiment, the foams and foam compositions are prepared as cartilage implants. In a preferred embodiment, the cartilage implants include a substrate including a biopolymer solution and a calcium phosphate cement which has set into a cement and a single or double density biopolymer foam embedded, e.g., by freeze-drying, in one face of the cementous substrate. The single or double density biopolymer foam of the cartilage implant can also be seeded with chondrocytes. In another embodiment, the foams and foam compositions are prepared as ligament implants. Typically, the ligament implants are composed of a plurality of biopolymer filaments and a single or double density biopolymer foam.

In a still further aspect of the invention, the foams and foam compositions are prepared as glandular implants. The glandular implants can be prepared from a foam or foam composition described herein and can include extracellular matrix particulates derived from glandular tissue. In a preferred embodiment, the glandular tissue can also be seeded with the appropriate glandular cells, e.g., pancreatic islet cells, hepatocytes.

DETAILED DESCRIPTION OF THE INVENTION

The present invention features biopolymer foams, composite biopolymer foams, biocompatible constructs comprising biopolymer foams and extracellular matrix particulates and methods for making and using these foams and foam compositions. A biopolymer is a polymer which is suitable for introduction into a living organism, e.g., a mammal, e.g., a human. Preferably, the biopolymer is non-toxic and bioabsorbable when introduced into a living organism and any degradation products of the biopolymer are also non-toxic to the organism. The biopolymers of the invention can be formed into biocompatible foams, e.g., single or double density foams, composite foams, and biocompatible constructs which include biopolymer fibers, e.g., collagen fibers, biopolymer fabrics, e.g., collagen fabrics, and/or extracellular matrix particulates. Examples of biopolymers which can be used in the present invention include collagen, alginic acid, polyvinyl alcohol, proteins, such as chondroitin sulfate, elastin, laminin, heparan sulfate, fibronectin and fibrinogen. In one embodiment, a combination or mixture of one or more biopolymers can be used to form the biopolymer forms, e.g., fibers, foams, and foam compositions of the invention. For example, a combination of chondroitin sulfate and fibronectin can be used to form the biopolymer fibers described herein. A preferred biopolymer is collagen.

Preferred sources of biopolymers include mammals such as pigs, e.g., near-term fetal pigs, sheep, and cows. Other sources of the biopolymers include both land and marine vertebrates and invertebrates. In one embodiment, the collagen can be obtained from skins of near-term, domestic porcine fetuses which are harvested intact, enclosed in their amniotic membranes. Collagen or combinations of collagen types can be used in the foams and foam compositions described herein. A preferred combination of collagen types includes collagen type I, collagen type III, and collagen type IV. Preferred mammalian tissues from which to extract the biopolymer include entire mammalian fetuses, e.g., porcine fetuses, dermis, tendon, muscle and connective tissue. As a source of collagen, fetal tissues are advantageous because the collagen in the fetal tissues is not as heavily crosslinked as in adult tissues. Thus, when the collagen is extracted using acid extraction, a greater percentage of intact collagen molecules is obtained from fetal tissues in comparison to adult tissues. Fetal tissues also include various molecular factors which are present in normal tissue at different stages of animal development.

The biopolymers can be used to create foams, e.g., single or double density foams, which can be in any form or shape, e.g., strips, sheets, tubes, etc. In addition, the biopolymers can be used to create foams which are then combined with polymer mesh, e.g., a teflon mesh, or used with tissue culture inserts for multiwell plates which can be used as molds in which foams and foam compositions of the invention can be formed for cell culture. Polymer meshes used with the foams and foam compositions of the invention can expose cells contained on and within the foams and foam compositions to the atmosphere as, for example, when the foams and foam compositions are used as skin equivalents to stimulate formation of a stratum corneum. Both the meshes and culture inserts have the advantage of providing a means for handling the foams and foam compositions without requiring actual contact with the foams or foam compositions. The forms and shapes in which the foams and foam compositions are made can mimic those of tissues or body parts to be replaced and thus can be used as prostheses or grafts which tissue cells remodel to promote regeneration of a replacement tissue in the recipient. Extracellular matrix particulates and/or viable cells can also be added to the biopolymers to further promote cell in growth and tissue development and organization within the foams.

The biopolymer foams can be single density or double density foams. As used herein, the term "foam" refers to a network of communicating microcompartments having biopolymer molecules and/or biopolymer filaments interspersed within the walls of the microcompartments. The language "single density foam" refers to a biopolymer foam having at least two of the following characteristics: 1) it has microcompartments with the volume dimensions of x, y, and z wherein x=length, y=width, and z=height and are substantially equal. Typically, x, y, and z range from about 1 $\mu$m to about 300 $\mu$m, preferably from about 20 $\mu$m to about 200 $\mu$m, more preferably from about 40 $\mu$m to about 150 $\mu$m, and most referably from about 50 $\mu$m to about 100 $\mu$m; 2) it has microcompartments with an average wall thickness of less than about 10 $\mu$m; 3) it has microcompartinents with walls which include biopolymer fibers and/or filaments; 4) it is physically stable in aqueous solutions; 5) it is nontoxic to living organisms; and 6) it can serve as a substrate for cell attachment and growth. The single density foams retain their structure when hydrated, for example, in aqueous buffer solution or tissue culture medium. In addition, the three dimensional structure of the single density foams can support the organization of cells seeded into them. Single density foams, when prepared from collagen and without cells, can be readily digested with collagenase, e.g., 0.1% collagenase. When hydrated, the height of the standard single density foams for research products is typically about 1 mm. Examples of single density collagen foam products specifications, e.g., sizes, collagen content, can be found in Table 1:

TABLE 1

EXAMPLES OF SPECIFICATION FOR SINGLE DENSITY FOAMS

| Diameter (mm) | Collagen Content (mg) | Form | Diameter of Polymer Mesh (mm) | Foam Will Fit Inserts Designed for These Multiwell Plates | Size of Multiwell plates for culture |
|---|---|---|---|---|---|
| 7 | 0.66 | 1. freestanding; or 2. bonded to polymer mesh. | 9 | 24 well plates | 96 well plates |
| 12 | 1.75 | 1. freestanding; or 2. bonded to polymer mesh. | 14 | 12 well plates | 24 well plates |
| 25 | 7.45 | 1. freestanding; or 2. bonded to polymer mesh. | 27 | 6 well plates | 12 well plates |

As used herein, the language "double density foam" refers to a biopolymer foam having at least two of the following characteristics: 1) it has microcompartments with the volume dimensions of x, y, and z wherein x=length, y=width, and z=height, two of which are substantially equal and the third of which is decreased or diminished by a factor of at least about 10, and more preferably at least about 20 or more compared to the same dimension in the single density foam, and can range from about 1 μm to about 300 μm, preferably from about 20 μm to about 200 μm, more preferably from about 40 μm to about 150 μm, and most preferably from about 50 μm to about 100 μm; 2) it has microcompartments with an average wall thickness of less than about 10 μm; 3) it has microcompartinents with walls which include biopolymer fibers and/or filaments; 4) it is physically stable in aqueous solutions; 5) it is nontoxic to living organisms; and 6) it can serve as a substrate for cell attachment and growth. The double density foams, when prepared from collagen, are resistant to collagenase digestion to a greater degree than single density foams made from collagen, e.g., from about 3 to about 5 times or more, more resistant to 0.1% collagenase than single density foams. Double density foams prepared from collagen also have a higher collagen density per unit volume than the collagen content per unit volume of single density foams. When hydrated, the height of the double density foams is typically from about 0.2 mm to about 0.4 mm. Either surface of the double density foam provides a substrate suitable for plating epithelial, endothelial, and mesothelial cells which can form sheets. Mesenchymal cells can also be seeded onto the double density foams. The double density foams can be produced in the same sizes and same forms, e.g., in any form and in combination and bonded to a polymer mesh or as a multiwell plate insert, as the single density foams. Cells grown on both the single and double density foams of the invention have morphologies characteristic of cells of three dimensional tissues and can form normal intercellular relationships, i.e., intercellular relationships like those in the tissue from which they are derived or obtained.

Single density foams of the invention can be produced by forming a biopolymer solution, freeze-drying the solution to form a biopolymer foam, and crosslinking the biopolymer foam. In another embodiment, the foam can be formed by performing the crosslinking step prior to the freeze-drying step. The step of freeze-drying converts the biopolymer solution into a foam, i.e., a network of communicating microcompartments with biopolymer molecules and/or filaments interspersed throughout its walls. When the foam is crosslinked, it becomes physically stable and insoluble in aqueous solutions. In a preferred embodiment, the biopolymer solution is polymerized prior to freeze-drying to form a biopolymer lattice. As used herein, a biopolymer lattice refers to a network of biopolymer filaments in which fluid is trapped. Biopolymer filaments are nanometer-sized forms of polymerized biopolymer molecules. For example, if the biopolymer is collagen, the collagen polymerizes into nanometer sized filaments by a process of self-assembly.

Double density foams having tensile strength which is greater than that of the single density foams can be produced by further processing of the single density foams. After a single density foam is freeze-dried, it can be hydrated with, for example, a sterile aqueous buffer. If the hydrated single density foam is to be further shaped to have a selected form, e.g., it can be molded or formed in, on, or around a desired shape, e.g., it can be molded around a mandrel to form a tubular shape or it can be sandwiched between a block and a screen separated by spacers of selected sizes, e.g., 0.5 mm. Shaped, hydrated single density foams and flat, hydrated single density foams are then dried, e.g., air dried, at a temperature not greater than about 37° C.–40° C. under sterile conditions. At temperatures greater than about 37° C., the biopolymer in the foams will begin to denature. The resulting double density foam has a selected thickness, e.g., about 0.2 mm if sandwiched with spacers of 0.5 mm as described above, and retains the fibers, walls, and two dimensional shape, but not the microcompartment sizes of the single density foams. The double density foam is stiff when dry and pliable when wet. It is resistant to tearing and to enzymatic digestion to a much greater extent that the single density foam. In contrast to the single density foam, the double density foam is a tight matrix which is preferred as a substrate for cells which normally grow on surfaces such as epithelial cells and endothelial cells. For example, the double density foam can be formed in the shape of a tube for use in reconstructing vessels or ducts or into a sheet and secured to large areas with sutures. Alternatively, the double density foam can be seeded with mesenchymal cells such as fibroblasts, muscle cells, chondrocytes, etc.

The double density foam, when prepared using collagen as the biopolymer, due to its increased collagenase resistance, can be used as a periodontal prosthesis to form a barrier to in growth of certain cells, e.g., epithelial cells that interfere with regeneration of periodontal tissue, while providing a substrate, in the form of the single density biopolymer foam, for the growth of the appropriate periodontal cells which eventually remodel and replace the foam product. In addition, a single density biopolymer foam and a double density biopolymer foam can be combined into a composite biopolymer product as different layers when the characteristics of each of the foams provide environments which favor, e.g., attract, growth of selected cell types. For example, when preparing a a composite foam for use as a skin equivalent or dressing, keratinocytes can be used to seed the double density foam while dermal fibroblasts can be used to seed the single density foam.

The biopolymer solution, which can be formed by treating the biopolymer in such a manner that it becomes soluble, e.g., by manipulating its pH to put it into solution, can be polymerized using methods of polymerization known in the art. For example, the biopolymer, e.g., collagen, can be polymerized to form a biopolymer lattice by manipulation of the pH of the biopolymer solution, e.g., by exposure to ammonium vapor or by adding base. As the pH of the solution reaches neutrality, the biopolymer polymerizes. The rate of polymerization is proportional to temperature and can be controlled by regulating the temperature of the collagen solution.

After the biopolymer has been polymerized to form a biopolymer lattice, it can be freeze-dried and/or crosslinked. Typically, the order of the these steps depends on the method of crosslinking used. For example, if the crosslinking method is a liquid phase method, e.g., use of lysyl oxidase to crosslink collagen, or use of aldehydic crosslinking methods, the crosslinking step is performed prior to the freeze-drying step. Alternatively, if the crosslinking method is a solid phase method, e.g., use of ultraviolet radiation, the crosslinking step is performed after the freeze-drying step. Crosslinking of the biopolymer can be accomplished by use of crosslinking methods known in the art. For example, the biopolymer can be crosslinked by subjection to ultraviolet radiation or by treatment with chemical crosslinking agents such as carbodiimide, glutaraldehyde, acetaldehyde, formaldehyde, and ribose. The biopolymer can also be crosslinked by dehydrothermal crosslinking.

In one embodiment, prior to freeze-drying, selected reinforcing material can be added to the biopolymer solutions. Such reinforcing materials include biopolymer fibers, threads, e.g., woven or braided threads, and/or fabrics, e.g., nonwoven fabrics, prepared, for example, by textile methods. Biopolymer threads, e.g., collagen threads, can be prepared by extruding the biopolymer in solution into a coagulation bath and transferring the biopolymer to a bath containing ethanol or acetone or another dehydrating solution. Alternatively, the thread can be dehydrated by subjection to vacuum-drying. The biopolymer thread can then be crosslinked by, for example, methods described herein. An example of an apparatus for spinning and processing a biopolymer fiber, e.g., collagen fiber, is described in U.S. Ser. No. 08/333,414, filed Nov. 2, 1994, the contents of which are incorporated herein by references in their entirety. The threads can then be dried, spooled, for example, by pulling the moving thread over more rollers, stretching and drying it and then winding it onto spools. The threads can be woven or braided into fabric or other complex forms or constructs for use as described herein.

Biopolymer fabrics, e.g., nonwoven biopolymer fabrics, are typically composed of a mat of entangled biopolymer fibers of a selected size and density. Typically, the nonwoven biopolymer fabrics are produced by spooling dry biopolymer fiber onto a drum of circumference equal to that of the length of an individual fiber element. Spooling is continued until the number of wraps of fiber on the drum equals the number of pieces of fiber required for the fabric. A cut is then made across the wound fiber in a direction parallel to the drum axis and the fibers are removed from the drum. The fiber can then be crosslinked if it has not been previously crosslinked. The fiber is then dispersed in a volume of a phosphate buffer solution for a period of time to decrease its pH and soften the fiber. The fiber is transferred to a volume of water and agitated mechanically to produce entanglement of the fiber strands. The entangled fiber strands are sieved from the water onto a collection screen until they coat the screen in a mat of uniform density. The mat is then dried on the screen or after transfer to another surface, screen, or cell culture device. If desired, the nonwoven mat can be cut or punched into smaller shapes after drying.

In one embodiment, when the biopolymer is collagen, the collagen can be treated with an enzyme, e.g., lysyl oxidase which primes the collagen for crosslinking. Lysyl oxidase, which can be purified from a variety of sources including, for example, calf aorta, human placenta, chicken embryo epiphyseal cartilage, pig skin, (see Shackleton, D. R. and Hulmes, D. J. S. (1990) *Biochem. J* 266:917–919), and several locations in pig embryos, converts the $\epsilon$-amino group of lysine to an aldehyde. This aldehyde is a reactive functional group which spontaneously binds to other lysine $\epsilon$-amino groups or other aldehydes on other collagen molecules to form irreversible covalent crosslinks. The result is that collagen becomes insoluble. Lysyl oxidase can be added to the collagen solutions under conditions which allow for the aldehyde conversion of the lysines. The lysyl oxidase is then removed from the collagen solution and the collagen is processed as described herein during which the spontaneous crosslinks form. For example, during the processing of the collagen foams, e.g., during the polymerization and freeze-drying steps, the crosslinks spontaneously form as the concentration of collagen per unit volume increases. The lysyl-oxidase-mediated crosslink is strong, irreversible and is a linkage naturally found in collagen. Collagen crosslinked in this manner is insoluble and susceptible only to specific enzymatic attack during remodeling of tissues. Lysyl oxidase can also be used to crosslink collagen for use as foams and foam compositions as well as spun fibers, gels, etc.

The biopolymer solution can then be freeze-dried to form a foam. In one embodiment, the freezing step is a controlled freezing step performed according to the method described in U.S. Pat. No. 4,531,373, the contents of which are incorporated herein by reference. The freeze-drying cycle typically includes freezing, evacuation, and drying phases. The freezing temperatures suitable for formation of the biopolymer foams of the invention depend upon the concentration of the biopolymer in solution or in the biopolymer lattice. Thus, for a collagen lattice in which the collagen is at a concentration of about 5 mg/ml the freezing temperature is typically less than $-26°$ C. The collagen lattice is exposed to this temperature for a period of about 1 hour. A vacuum is then applied to the collagen lattice as the temperature is slowly raised.

To prevent the formation of fissures in the foam and thus to allow for greater foam size, an anti-freeze polypeptide (AFP) or an anti-freeze glycoprotein (AFGP) can be added to the biopolymer solution prior to or during the freezing step. Examples of AFPs include the AFPs which belong to the AFP Types I, II, and III. For a detailed description of the different types of AFPs, see, e.g., U.S. Pat. No. 5,358,931, PCT publication WO 92/12722, and PCT publication WO 91/10361, the contents of which are incorporated herein by reference. These polypeptides and glycoproteins prevent the formation of large ice crystals during freezing of the biopolymer solution and also prevent the formation of crystals of recrystallization during the drying process. Large ice crystals can create fissures in the resulting foam which contribute to poor crosslinking and splitting of the foam. Use of AFPs and AFGPs allow for the formation of a pore structure which has connected channels and thus allows for cohesion of the various sections of the foam. This feature improves the quality of the foams and enables the production of large foams. For example, when an AFP or combination of AFPs is freeze-dried with the biopolymer in high concentrations, e.g., about 0.2 to 0.5 mg/ml (about 124 $\mu$M), it dramatically reduces the normal foam pores until the foam resembles tightly packed long fibers. The foams produced using the AFPs in the freezing cycle can be employed, for example, as implants which direct specific cellular processes, e.g., through growth along the fibers.

In a preferred embodiment, the biopolymer solution is a collagen solution. The collagen used in this solution can be produced by salt extraction, acid extraction, and/or pepsin extraction from the starting material. In a preferred embodiment, the collagen used in this solution is produced by sequentially purifying two forms of collagen from the same collagen-containing starting material. First, intact collagen is acid extracted from the starting material. Next, truncated collagen, i.e., collagen from which the telopeptides have been cleaved leaving only the helical portion, is extracted from the starting material using enzyme, e.g., an enzyme which is functional at an acidic pH, e.g., pepsin, extraction. The extracted collagen can then be prepared as a collagen solution, e.g., by precipitating the collagen with sodium chloride and solubilizing the collagen in a medium having an acidic pH.

The single and double density biopolymer foams of the invention can be combined to form composite biopolymer foams. Thus, composite biopolymer foams of the invention include at least one layer of a single density biopolymer foam and at least one layer of a double density foam. Either or both of these foam layers in the composite foam can be conditioned with cells prior to use of the composite foam in vitro or in vivo. The composite biopolymer foams are typically produced or prepared by providing a double density biopolymer foam, which is produced as described herein, hydrating the double density biopolymer foam and then adding a biopolymer solution to the double density biopolymer foam. The double density biopolymer foam together with the biopolymer solution is freeze-dried to form a composite biopolymer foam.

Biocompatible constructs which include biopolymer foams of the invention and extracellular matrix particulates are also specifically contemplated herein. Extracellular matrix particulates or extracellular matrix particulates dispersed or suspended in a biopolymer solution can also be applied onto and/or into the foams and foam compositions of the invention, thereby forming a foam having extracellular matrix particulates. As used herein, the language "extracellular matrix particulate" refers to a fragment of an extracellular matrix derived from a tissue source formerly having living cells but which has been processed to remove the cells and to retain noncellular extracellular matrix factors such as, for example, growth factors necessary for cell growth, morphogenesis, and differentiation. Methods for forming extracellular matrix particulates for producing graft tissue are disclosed in U.S. patent application Ser. No. 07/926,885, filed Aug. 7, 1992, U.S. patent application Ser. No. 08/302,087, filed Sep. 6, 1994, and U.S. patent application Ser. No. 08/471,535, filed Jun. 6, 1995. The teachings of U.S. patent application Ser. Nos. 07/926,885, 08/302,087, and 08/471,535 are incorporated herein by reference.

The methods for forming extracellular matrix particulates include freezing a tissue source, e.g., a connective tissue source, having living cells, whereby the living cells are disrupted to form cell remnants consisting of, for example, cytoplasmic and nuclear components. The tissue source is then processed, e.g., by grinding, washing and sieving, to remove the cytoplasmic and nuclear components without removing extracellular matrix including factors necessary for cell growth, migration, differentiation, and morphogenesis. The extracellular matrix is freeze-dried and fragmented, e.g., cryomilled to produce particulates of defined sizes, to produce extracellular matrix particulates.

The extracellular matrix particulates can include extracellular matrix proteins. For example, extracellular matrix particulates obtained from skin include transforming growth factor $\beta 1$, platelet-derived growth factor, basic fibroblast growth factor, epidermal growth factor, syndecan-1, decorin, fibronectin, collagens, laminin, tenascin, and dermatan sulfate. Extracellular matrix particulates from lung include syndecan-1, fibronectin, laminin, and tenascin. The extracellular matrix particulates can also include cytokines, e.g., growth factors necessary for tissue development. The term "cytokine" includes but is not limited to growth factors, interleukins, interferons and colony stimulating factors. These factors are present in normal tissue at different stages of tissue development, marked by cell division, morphogenesis and differentiation. Among these factors are stimulatory molecules that provide the signals needed for in vivo tissue repair. These cytokines can stimulate conversion of an implant into a functional substitute for the tissue being replaced. This conversion can occur by mobilizing tissue cells from similar contiguous tissues, e.g., from the circulation and from stem cell reservoirs. Cells can attach to the prostheses which are bioabsorbable and can remodel them into replacement tissues.

Growth factors necessary for cell growth are attached to structural elements of the extracellular matrix. The structural elements include proteins, e.g., collagen and elastin, glycoproteins, proteoglycans and glycosaminoglycans. The growth factors, originally produced and secreted by cells, bind to the extracellular matrix and regulate cell behavior in a number of ways. These factors include, but are not limited to, epidermal growth factor, fibroblast growth factor (basic and acidic), insulin-like growth factor, nerve growth-factor, mast cell-stimulating factor, the family of transforming growth factor-$\beta$, platelet-derived growth factor, scatter factor, hepatocyte growth factor and Schwann cell growth factor. Adams et al., "Regulation of Development and Differentiation by the Extracellular Matrix" *Development* Vol. 117, p. 1183–1198 (1993) (hereinafter "Adams et al.") and Kreis et al. editors of the book entitled "Guidebook to the Extracellular Matrix and Adhesion Proteins," Oxford University Press (1993) (hereinafter "Kreis et al.") describe extracellular matrix components that regulate differentiation and development. Further, Adams et al. disclose examples of association of growth factors with extracellular matrix proteins and that the extracellular matrix is an important part of the micro-environment and, in collaboration with growth factors, plays a central role in regulating differentiation and development. The teachings of Adams et al. and Kreis et al. are incorporated herein by reference.

Extracellular matrix particulates can be obtained from specific tissues. The particulates have two kinds of informational properties. The first is their molecular diversity, and the second is their microarchitecture, both of which are preserved in the preparation of the microparticulates. The preferred associations among the different molecules of the extracellular matrix are also preserved in the preparation of the microparticulates.

The extracellular matrix plays an instructive role, guiding the activity of cells which are surrounded by it or which are organized on it. Since the execution of cell programs for cell division, morphogenesis, differentiation, tissue building and regeneration depend upon signals emanating from the extracellular matrix, three-dimensional scaffolds, such as collagen foams, are enriched with actual matrix constituents, which exhibit the molecular diversity and the microarchitecture of a generic extracellular matrix, and of extracellular matrices from specific tissues.

To provide further cellular and molecular binding sites on the surfaces of the foams and foam compositions to replace, for example, binding sites which have been compromised as a result of crosslinking procedures, a coating process can precede or accompany the application of extracellular matrix particulates to the collagen foam. In addition, artificial microstructures, typically having a size in the range of between about 5 and 500 $\mu$m, composed of a matrix polymer, such as collagen, combined with other proteins, proteoglycans, glycosaminoglycans, extracellular matrix enzymes, cytokines (including growth factors), and glycosides can be created in the form of wet or dry particulates that can be applied with the coating solution to the surfaces of the collagen foam. The selected components can be chemically or electrostatically bound to the biopolymer or can be contained in the microparticulate lattice or in a dehydrated form of the lattice. Thus, the invention also pertains to methods for preparing collagen-coated foams and extracellular matrix particulate-coated foams. These methods typically include forming the selected type of biopolymer foam as described herein and applying a collagen solution or an extracellular matrix particulate solution to the freeze-dried foam, thereby forming the collagen-coated or extracellular matrix particulate-coated biopolymer foam. The coated foams can be further freeze-dried. In one embodiment, the collagen solution also includes extracellular matrix particulates.

The foams and foam compositions of the present invention can be used as substrates for cell growth in vitro and in vivo, e.g., for establishing research model systems. For example, in one embodiment, the foams and foam compositions can be seeded with abnormal cells to study disease states including cancer. In another embodiment, the foams and foam compositions can serve as diagnostic test models for determining chemotherapeutic strategies by selecting for agents capable of killing cancer cells cultivated in or on the foams. In yet another embodiment, the foams and foam compositions can be used to test the toxicity of various substances to which cells in or on the foams are exposed.

The foams and foam compositions can also be used as prostheses which can be introduced or grafted into recipients, e.g., such as mammalian recipients, e.g., humans. For example, the foams and foam compositions can be used as a prosthesis or to reconstitute, for example, the following types of tissue: nervous tissue, skin, vascular tissue, muscle tissue, connective tissue such as bone, cartilage, tendon, and ligament, kidney tissue, liver tissue, and pancreatic tissue. Tissue cells seeded into these foams and foam compositions can be obtained from a mammal, e.g., a human. Tissue cells are delivered to the foams and foam compositions by first suspending the cells in small volumes of tissue culture medium. The tissue culture medium which contains the cells can then be applied in drops to the foams or foam compositions. Alternatively, the foams or foam compositions can be placed in a vessel which contains the tissue culture medium and cells in suspension and which shakes such that the tissue culture medium containing the cells is distributed throughout the foams and foam compositions. In another embodiment, tissue cells can be suspended in a biopolymer solution e.g., a collagen solution, at low concentrations, at a temperature of about 4° C. to 10° C., and at a pH of about 7.0. The solution containing the cells can then be delivered to the foams and foam compositions. As foam is warmed to 37° C., the biopolymer solution, e.g., collagen solution, forms a gel in the foam. As used herein, the term "gel" refers a network or mesh or biopolymer filaments together with an aqueous solution trapped within the network or mesh of biopolymer filaments. An alginate gel for use as a delivery vehicle of cells to the foams or foam compositions of the invention can be produced by addition of calcium which causes polymerization at room temperature and at a neutral pH. Selected epithelial, endothelial, or mesothelial cells can then be plated onto the surface of the gel-filled foam or foam composition.

The foams and foam compositions of the invention can be used as skin dressings for burns, scars, and skin ulcers and lesions. For example, a composite biopolymer foam comprising a single density biopolymer, e.g., collagen, foam is attached to a surface of a double density biopolymer foam to produce a full thickness skin dressing which can further include cell conditioning, e.g., dermal and epidermal cell conditioning. The composite biopolymer foam can be prepared by first preparing the double density biopolymer foam as a sheet from which disks or other shapes can be punched out, or by preparing the double density biopolymer foam in a mold of the desired shape and size. The double density biopolymer foam can then be placed in the bottom of a mold of the same geometry and dimensions as that of the double density biopolymer foam and hydrated, e.g., with an aqueous buffer, e.g., MilliQ™ water or a biopolymer, e.g., collagen, solution. The mold is then filled with liquid biopolymer, e.g., collagen, to the height required for the single density foam and the combination is freeze-dried as described herein to produce a skin dressing. In one embodiment, the single density biopolymer foam layer is seeded with dermal fibroblasts, e.g., human dermal fibroblasts, e.g., autogenous human dermal cells (i.e., dermal cells donated by the skin dressing recipient), e.g., allogeneic human dermal cells (i.e., dermal cells provided by a donor of a different genotype than that of the graft recipient) and incubated for at least one day or more days, e.g., from about four to about seven days. The double density biopolymer foam layer is seeded with keratinocytes, e.g., human keratinocytes. The keratinocytes are allowed to differentiate until a barrier-competent stratum corneum is formed, e.g., for about fourteen days. The presence of the dermal cells allows for the full differentiation of the epidermis. This period of development allows time for enrichment of the dermal and epidermal tissues of the foam product with extracellular matrix products, e.g., extracellular matrix products secreted by the dermal fibroblasts. The composite biopolymer foam is then processed, e.g., freeze-dried, to eliminate the cells. The resulting cell-conditioned composite biopolymer foam has the properties of full thickness skin and can be used as a skin dressing to, for example, treat burns, scars, and skin ulcers and lesions. This product serves, particularly in the case of burns, e.g., third degree burns, to reduce loss of body moisture when applied as a skin dressing and is convenient for use in emergency situations in which the recipient of the skin injury is not nearby professional health care providers. When placed on a recipient requiring a skin graft, the foam product, with or without cell conditioning, becomes populated with host (graft recipient) fibroblasts and keratinocytes. Fibroblasts and capillary endothelium from the dressing recipient or host can migrate into the composite biopolymer foam. The composite biopolymer foam also provides a substrate for keratinocytes seeded or plated on it and allows keratinocytes to spread on and within it from adjacent skin or from below, e.g., from hair follicles that can remain after the skin injury. Alternatively, the foam product can serve as a substrate for cultured autogenous or allogeneic keratinocytes. These freeze-dried composite biopolymer foams, which can be seeded with a selected cell type, have long half-lives and thus can be stored for long periods of time.

In another embodiment, a double density foam can serve as a skin dressing. The double density foam is first seeded with dermal cells in tissue culture medium (with or without collagen, e.g., collagen at 1 mg/ml). After several days, epidermal cells, e.g., keratinocytes, are seeded onto the surface of the foam which is already populated with dermal cells. The cells in and on the double density foam are then allowed to divide, differentiate, and form a skin-like organ in vitro. The foam is then freeze-dried after a period of several weeks in vitro. The resulting foam scaffold is resistant to breakdown by microbial collagenase and has a well-developed stratum corneum.

The foams, foam compositions, and other forms of biopolymers described herein can be conditioned, e.g., contacted or exposed to cells, with cells. For example, the foams, foam compositions, and other forms of biopolymers can be seeded with a selected cell type or selected cell types. The cells can then be allowed to grow, proliferate, and secrete factors, e.g., extracellular matrix factors, that support, for example, cell growth, differentiation, morphogenesis. The cell conditioning of the foams, foam compositions, and other biopolymer forms described herein serves at least two functions. First, the cells provide chemical conditioning of the foams, i.e., the cells secrete extracellular matrix components which attract in growth of cells into the foams, foam compositions, and biopolymer forms and support the growth and differentiation of the cells in the foams. Second, the cells provide mechanical conditioning of the foams, foam compositions, and biopolymer forms, i.e., the cells remodel the foams, foam compositions, and biopolymer forms to form a scaffold which provides the appropriate physical structure for the type of cells in the tissue which the foam is to replace or reconstruct, e.g., the cells arrange themselves in the different cells layers of the skin as described herein. The foams, foam compositions, and biopolymer forms containing viable cells can be introduced into a recipient subject. Alternatively, the foams, foam compositions, and biopolymer forms containing the cells can be further processed to kill the cells, e.g., freeze-dried, and then introduced into a recipient subject.

The foams and foam compositions of the invention can also be formed into vascular prostheses in the form of a tube and can be seeded internally with smooth muscle cells delivered in a neutralized collagen solution that gels after delivery, externally with adventitial fibroblasts and on its luminal surface with endothelial cells. For example, a vascular prosthesis or a vascular stent can be formed by casting a double density biopolymer foam layer around a mandrel. The prosthesis or stent is then formed by sealing the mandrel into a tube with a space between the outside of the mandrel and the inside wall of the tube. If the biopolymer is collagen, the tube is then filled with lysyl oxidase primed collagen to bring about crosslinking of the collagen during processing. The collagen-coated mandrel is freeze-dried on a shelf in a freeze dryer which follows a program of controlled drying. Alternatively, the collagen or a different biopolymer can be crosslinked using ultraviolet radiation. The foam is hydrated under vacuum and allowed to dry to form a double density foam. After drying, the double density foam is removed from the mandrel in the form of a tube for use as a vascular prosthesis. The double density foam can be reinforced by winding a crosslinked biopolymer thread, e.g., wound collagen thread (the reinforcing material), around the double density foam layer and then casting a single density biopolymer foam layer or a second double density biopolymer foam layer over the wound thread. The two layers of double density foams are then fused such that the wound biopolymer thread is incorporated into the resulting tubular shaped foam. If desired, medial smooth muscle cells and endothelial cells are then delivered to the abluminal and luminal surfaces, respectively, of the tubular foam. A layer of adventitial fibroblasts can then be added onto the medial smooth muscle cells. The tubular foam can be treated in vitro to obtain a vessel having the structure of a mature blood vessel. For example, the tubular foam together with these cell layers can be subject to pulsatile flow of increasing magnitude of a selected fluid, e.g., glycerol and culture medium to result in a mature blood vessel, for use, for example, as a vascular prosthesis or stent.

For rebuilding bone, cartilage, tendon, and ligament, the foams and foam compositions of the invention can be seeded with the appropriate cells, e.g., connective tissue cells such as osteocytes, chondrocytes, and tendon and ligament fibrocytes, and molded in the appropriate form to repair damaged connective tissue. In one embodiment, the biopolymer foams of the invention, with or without extracellular matrix particulates, can be mixed with calcium phosphate cement, e.g., β-tricalcium phosphate cement which includes 64% β-tricalcium phosphate, 16% calcium phosphate monobasic, 15% calcium sulfate hemihydrate, and 5% calcium pyrophosphate (see Mirtichi et al. (1989) *Biomaterials* 10:634–638) to produce a reinforced cement for use as, for example, orthopedic or dental implants. Gelatin, a derivative of collagen which constitutes much of the organic content of bone, can be added to the calcium phosphate cement as an adhesive. In another embodiment, the biopolymer foams of the invention are cast onto the cement and processed as described herein. Alternatively, the extracellular matrix particulates described herein can be mixed with calcium phosphate cement and used as orthopedic or dental implants. The biopolymer foams and/or extracellular matrix particulates increase bone cell invasion of the calcium phosphate cement. In addition, growth factors present in the extracellular matrix particulates provide mitogenic stimuli to increase the rate at which the bone cells multiply and replace the cement. For example, it has been found that extracellular matrix particulates from a variety of tissues, when added to culture inserts, stimulated mitosis in a variety of different cell types when compared to culture inserts without the extracellular matrix particulates. See Table 2 which shows the results of experiments in which 1 mg of extracellular matrix particulates from the indicated tissue origin were added to culture inserts containing the indicated cell types in serum-free medium. After five days, the cell number in the cultures containing the extracellular matrix particulates and the cell number in the control cultures without the extracellular matrix particulates was determined.

TABLE 2

MITOGENIC EFFECT OF EXTRACELLULAR MATRIX PARTICULATES ON SELECTED CELL TYPES

| Tissue Origin of Extracellular Matrix Particulates | Cell Type | Percent of Control Cell Number |
|---|---|---|
| Skin | dermal fibroblasts | 380 |
| Skin | intestinal smooth muscle cells | 150 |
| Lung | dermal fibroblasts | 250 |
| Liver | dermal fibroblasts | 220 |
| Muscle | dermal fibroblasts | 350 |
| Small intestine | dermal fibroblasts | 120 |
| Small intestine | aortic smooth muscle cells | 150 |
| Small intestine | intestinal smooth muscle cells | 170 |
| Heart | dermal fibroblasts | 370 |
| Heart | aortic smooth muscle cells | 150 |
| Heart | intestinal smooth muscle cells | 190 |
| Bladder | dermal fibroblasts | 230 |
| Kidney | dermal fibroblasts | 400 |

The biopolymer solutions, foams and/or extracellular matrix particulates as well as biopolymer fibers, e.g., braided fibers, and biopolymer fabrics can also increase the strength of the calcium phosphate-based cement by at least about 20%, at least about 30%, at least about 40%, and preferably at least about 50% or more if mixed with the cement in appropriate proportions. For example, when liquid collagen is added in the proportion of 5 mg of collagen to 8 g of cement or when extracellular matrix particulates are added in the proportion of 0.1 g extracellular matrix particulates to 8 g cement, the strength, as measured by pounds resisted until the cement breaks, of the cement increase 50% over that of cement without collagen or extracellular matrix particulates.

Cartilage implants are additional examples of implants which can be produced using the foams or foam compositions of the invention. In one embodiment, cartilage implants are generated by combining a biopolymer, e.g., collagen, solution with calcium phosphate cement and allowing the mixture to set (but not dry) into a cement. While the cement is still plastic and malleable, a biopolymer solution is cast onto the set but not dry cement and freeze-dried to form a layer of single or double density biopolymer foam embedded in one face of the cementous substrate. After the cement has set and dried, the biopolymer foam is seeded with chondrocytes. In an alternative embodiment, cartilage implants are produced by combining a biopolymer, e.g., collagen, solution with calcium phosphate cement and allowing the mixture to set and dry into a cement. The set and dry cement can then be rehydrated and saturated with biopolymer solution. A biopolymer solution can then be cast onto the cementous substrate and the assembly of the layer of biopolymer solution and the cementous substrate is freeze-dried to form a layer of single or double density biopolymer foam embedded in one face of the cementous substrate. The biopolymer foam can then be seeded with chondrocytes, e.g., human chondrocytes (e.g., at $5 \times 10^4$–$5 \times 10^6$ cells/ml of foam). In either embodiment, the chondrocytes are allowed to differentiate and create a matrix typical of cartilage tissue and then are placed in an articulating relationship. Typically, an articulating relationship for the cartilage implant is established using a mechanical device for growing and developing articular cartilage. Such a mechanical device places the biopolymer foam containing the chondrocytes into gentle contact with a second surface, e.g., a second biopolymer foam containing chondrocytes, in the presence of fluid having similar characteristics as those of synovial fluid and which contains hyaluronic acid, e.g., a dialysate of blood plasma, such that it becomes a thixotropic fluid, i.e., a gel which liquefies when agitated but which reverts to a gel upon standing. The biopolymer foam containing the chondrocytes and the second surface are then rotated or slid across one another to create shear and compressive forces which mimic those to which cartilage tissue is exposed in vivo. The resulting cartilage tissue has the properties of normal articular cartilage tissue, e.g., the ability and architecture to withstand forces to which normal cartilage tissue is exposed.

Ligament implants, as multifilament forms of the biopolymers of the invention, can be enhanced with the foams and foam compositions of the invention to promote cell seeding. For example, continuous ligament multifilament structures can be produced with or without the addition of extracellular matrix particulates, to have selected characteristics. Ligament cells can then be delivered to the ligament which can be embedded in a foam casing. The ends of the ligament can be cut and embedded in calcium phosphate cement. The ligament can then be mounted in a tubular tissue maturation chamber. After the ligament cells have attached to the ligament, the ligament is subjected to a regime of cyclical axial elongation resulting in stress, which is increased in magnitude as the ligament matures. The mature biopolymer ligaments can be used, for example, as ligament prostheses.

Dental implants can be formed from the foams and foam compositions of the invention. For example, the foams and foam compositions can be prepared as specialized dental implants for periodontal ligament repair and bone rebuilding. In one embodiment, the foams and foam compositions of the invention are prepared as apron shaped implants which can be fixed to a tooth by tying the strings of the apron around the tooth. In another embodiment, the foams and foam compositions are designed as covers of post extraction sockets filled with calcium phosphate cement or collagen composition which is reinforced with calcium phosphate cement. In yet another embodiment, the foams and foam compositions are designed as calcium phosphate- or hydroxyapatite-filled tubes to serve as alveolar ridge builders.

The apron shaped foam, which can be produced as a double density or quadruple density foam, i.e., a double density foam folded over on itself, for promoting periodontal ligament repair and bone rebuilding can be positioned between a gum flap and the alveolar bone in the area requiring periodontal ligament repair and bone rebuilding. The foam can be designed to block invasion by junctional epithelium of the cleaned and planed tooth zone. Periodontal ligament cells can then migrate into the foam, bind to the foam, and secrete extracellular matrix products into the foam. The foam can also be invaded by capillary endothelial cells and immune cells which provide defense against microbial assault. By excluding epithelium and by stimulating periodontal ligament cells, the foam can promote regeneration of periodontal ligament and alveolar bone. The apron shaped dental implants can also be modified to include a calcium phosphate cement as described herein. In one embodiment, the calcium phosphate cement can be included in an outpocketing of the apron which can be placed on the eroded alveolar bone. The calcium phosphate cement provides pathways for invading bone cells and hardens when hydrated. The apron shaped dental implant can also include extracellular matrix particulates generated from dental tissues. These extracellular matrix particulates provide the appropriate growth factors, e.g., bone and ligament specific growth factors, for promoting periodontal ligament cell and bone cell growth into the implant.

Alternatively, the foams and foam compositions of the invention can be prepared as post extraction socket fillers. The foams can be mixed with calcium phosphate cement and inserted into sockets of extracted teeth. These socket fillers promote bone regeneration within the socket which, at a minimum, provides a foundation for a metal, e.g., titanium, fixture and subsequent application of a crown. The titanium or other material fixture can be anchored in a socket immediately after an extraction with calcium phosphate cement reinforced with one of the foam or foam compositions described herein. The implant can then be covered or "tented" with a double or quadruple double density foam membrane described herein as an apron. The socket fillers can also include extracellular matrix particulates generated from bone tissue or dental papilla. These extracellular matrix particulates provide the appropriate growth factors, e.g., bone specific growth factors, for promoting bone cell growth into the implant. In addition, in instances where the bony foundation for dental implants composed of metal does not provide adequate support for the metal implant, calcium phosphate cement reinforced or strengthened with the foams and foam compositions of the invention can be used to reinforce the bony foundation.

In yet another embodiment, the foams and foam compositions can be designed as alveolar ridge substitutes or alveolar ridge builders. Alveolar ridge substitutes are used to provide underpinning for dentures. Typically, the alveolar ridge substitutes are designed as double density foam tubes of the appropriate length which are filled with non-resorbable hydroxyapatite (or with the calcium phosphate cement described herein) to build up a mineralized platform along the alveolar ridge and to promote development of bone and a connective tissue framework around the hydroxyapatite particles. The alveolar ridge builders of the invention have the same design as that of the alveolar ridge substitutes except that the foam tube is filled with calcium phosphate cement which promotes bone development but which is resorbable. The composition of the alveolar ridge builders promotes bone cell and blood capillary penetration leading to regrowth and restoration of the ridge prior to, for example, installation of a denture or a metal implant. The foam tube of the alveolar ridge builder can also include extracellular matrix particulates which promote alveolar ridge bone regeneration.

Similarly, the foams and foam compositions of the invention enriched, for example, with extracellular matrix particulates derived from glandular tissue, e.g., pancreatic tissue, hepatic tissue, skin tissue, and other glandular tissue, can be seeded with glandular cells such as those of the endocrine pancreas, e.g., pancreatic islet cells, or those of the liver, e.g., hepatocytes, as means of promoting cell proliferation before and/or after implantation so that after implantation and vascularization of the cell-laden foam implant, a functional replacement gland develops.

Examples of cell types which have been successfully grown in and on the foam and foam compositions of the invention include mesenchymal cells, periodontal ligament cells, fibroblasts, keratinocytes, chondrocytes, gingival fibroblasts, and tendon and ligament cells.

This invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLE 1

Acid Extraction of Collagen from Skin of Porcine Fetuses

In a preferred method for extracting the collagen from tissue, a collagen source includes porcine fetuses. The fetuses are frozen in utero with the uteri maintained in an unbroken condition with the ends tied off by string. Twelve to twenty-four hours before dissection, a uterus is removed from the freezer and placed in a 4° C. cold room. The uterus, which should still be about 90% frozen, is transferred into a large sterile dishpan. As soon as possible, the folded uterus is gently straightened. The exterior surface of the uterus is washed twice for ten minutes in 1% bleach in Milli-Q™ water and is then washed twice with sterile Milli-Q™ water to sterilize the uterus exterior.

Under clean-room conditions, the entire length of the uterus on the surface opposite the major blood vessels is opened. Care is taken not to touch or damage the amniotic membranes of the fetus. Instruments that come in contact with the outer surface of the uterus are washed with 70% ethyl alcohol. Each fetus is gently lifted from the uterus and the umbilicus is cut at least two centimeters from the fetus. The still mainly frozen fetus is placed into a sterile plastic bag after the head is removed.

With sterile gloves, the fetus is transferred to a sterile glass dish. With a sterile scalpel, such as a #11 blade, the skin around each foot is sliced to make a circular incision. A single incision is made through the skin from the first cut, along the inner surface of each limb to the midline of the ventral surface of the trunk. A midline incision is made along the ventral surface of the trunk from the tail to the neck, taking care not to penetrate the underlying muscle tissue. The body skin is peeled off. The peeled skin is placed into a sterile container (one liter centrifuge bottle with cap) on ice.

The skins are ground with sterile ice, and the ground tissue is washed in ice cold 0.33×phosphate buffered saline (PBS): 5 liters, 9 washes of each 5 kg batch. The tissue is evenly divided into 20 liter carboys as required and each filled with 0.5 M acetic acid and 2 mM EDTA. The carboys are placed on a roller bottle apparatus for about seven days at a temperature of about 4° C.

On the eighth day after the beginning of the skin preparation, the skin and extract are separated by filtration through four layers of sterile cheese cloth. Sterile sodium chloride is added to bring the solution to about 0.9 M. It is stirred over a period of about two hours while the collagen forms a precipitate. The entire salt precipitated solution and the precipitate are centrifuged by continuous flow at 12,000 rpm 300 ml/min. The supernatant is discarded and the pellet is kept. The pellets are homogenized and dispersed in 0.5 M acetic acid having a pH of 2.5 plus 2 mM EDTA and transferred to a carboy on a rollerbottle apparatus for about sixteen hours at a temperature of about 4° C. The flask is checked for degree of solubilization and resuspension. More 0.5 M acetic acid and EDTA solution may be added to ensure complete dissolution of the pellet.

Sterile sodium chloride is added to the flask to bring the solution to about 0.9 M. It is stirred over a period of two hours to allow the collagen to precipitate for a second time as described above. The entire salt precipitated solution and the precipitate are centrifuged by continuous flow at 12,000 rpm 300 ml/min. The supernatant is filtered to 2.0 $\mu$m. The collagen concentration is then determined with a hydroxyproline assay. The solution is then dialyzed to 0.05M acetic acid and a concentration to 7 mg/ml in a hollow fiber. The final concentration of collagen is then determined using a hydroxyproline assay.

EXAMPLE 2

Sequential Acid and Enzyme Extraction of Collagen from Skin of Porcine Fetuses

Fetal porcine skin isolated as described in Example 1 is ground and washed, then mixed with a defined proportion of 0.5M acetic acid, 0.002M EDTA, pH 2.5 for eight days. The ground material is then separated from the liquid and intact collagen is purified from the liquid by two cycles of salt precipitation and dissolution as described in Example 1. The ground material is then mixed with 0.017% pepsin in 0.5M acetic acid, 0.002M EDTA, pH 2.5 for five days. The skin is again mixed with 0.017% pepsin in the same buffer for seven days. The ground material is again separated from the liquid. Slightly clipped collagen is then purified from the two liquid extracts by a similar method as acid extracted collagen. Both types of collagen are dialyzed into 0.05M acetic acid and concentrated to desired levels using hollow fiber filters of porosities which prohibit collagen from exiting. As determined by polyacrylamide gel electrophoresis, the acid extracted collagen is a mixture of fetal collagens including collagen type I, collagen type III, and collagen type IV. The pepsin extracted collagen, i.e., slightly clipped collagen, contains the triple helical cores without the telopeptides of the mixed collagens except for lower amounts of type IV, which is subject to degradation with the enzyme treatment. Collagen concentrations also are determined by Sirius Dye Assay calibrated by hydroxyproline assay standards. Protein identities and integrity are validated by polyacrylamide gel electrophoresis and viscosity is standardized at 5 mg/ml at a minimum of 50 centipoise. The collagen is able to form a gel at neutral pH. The absence of denatured contaminants is measured by polarity (values at −350° and lower are acceptable). Quality is also tested by the ability of the collagen to form fibers.

EXAMPLE 3

Production of Single Density Foam from Collagen Extracted from Skins of Porcine Fetuses A biopolymer solution (with or without extracellular matrix particulates) prepared as described in Example 1 or Example 2 is introduced into a well or other mold. Before introduction into the well, the collagen solution is degassed under vacuum until no further bubbling is observed. In one embodiment, the solution is exposed to 5–10 mm Hg for about one hour. The well is filled with an amount of polymer determined by the thickness of the foam product required. A well of about 1.2 cm diameter is filled with 0.35 milliliters of solution to provide a foam of about 2 mm in thickness. The well can be of any size and shape to produce the required geometry of freeze-dried product. The concentration of the bio-polymer in each well can be in the range of between 1.0 mg/ml of collagen to about 10 mg/ml depending on the density of product required. In a preferred embodiment, a solution having a concentration of about 5.0 mg/ml is used. While the collagen solution can be freeze-dried directly from the liquid state, in a preferred embodiment, the collagen solution is polymerized by exposure to an ammonium hydroxide vapor from a 29% solution, or by the addition of a base to the solution to form a pH of 7.0 while forming a gel. The rate of polymerization is proportional to temperature and can be controlled by regulating the temperature of the collagen solution in the well.

After polymerization of the solution and formation of a collagen lattice, the lattice is crosslinked by ultraviolet radiation at a wavelength of about 254 nm either before or after freeze-drying. If crosslinked before freeze-drying, the intensity of irradiation can be about $0.38 \times 10^7$ microjoules/$cm^2$. If crosslinked after freeze-drying, the intensity can be about four times the previous value. Exposure to ultraviolet radiation can be increased depending on the degree of crosslinking desired. Chemical crosslinking with 15 millimolar carbodiimide in 0.5×PBS can also be used.

The freeze-drying routine used to form a foam consists of a freezing, evacuation, heating cycle, which is varied as a function of polymer concentration since the eutectic temperature, i.e., the minimum freezing point for the entire volume of material being frozen, will vary with the concentration of biopolymer in solution or in the polymerized lattice.

Foam discs of the unfinished or finished dimensions 1.0–1.2 cm in diameter and 1.0–5.0 mm or greater in thickness can be inserted into multiwell plate transwells or in wells of tissue culture dishes or multiwell plates used for carrying out cell cultures. The foam inserts, inserted into transwell containers can be of any of the four types described above: that is uncoated with collagen solution, coated with collagen solution or coated with collagen solution containing extracellular matrix components in any of the forms described above. Each foam disc is seeded with tissue cells in a tissue culture medium. The types of cells selected to occupy the interstices of the foam, which is an open cell foam, are normally surrounded by extracellular matrix. In one embodiment, the tissue cells are mixed in a solution of neutralized collagen so that the cells become surrounded by a collagen gel in the foam. In this embodiment, cells of other phenotypes, in particular endothelial, epithelial or mesothelial can be plated on the under surface of the gel or on the upper surface of the gel, thereby constituting tissue equivalents of two, or three or more cell types. In another embodiment, the cells are placed in tissue culture medium.

Foam sheets, tubes, rods, cups and other shapes in the form of prostheses treated as described above with the various types of collagen solutions containing extracellular matrix components can be used as human replacement parts. For example, a 1.0 $cm^2$ rectangle having a thickness of about 0.4 millimeters provided with a crosslinked collagen apron string can serve as a periodontal prosthesis. In this instance, all the surfaces of the foam are decorated with extracellular matrix particulates from dental tissues. The particulates are tested for selected extracellular matrix components and are shown to contain basic fibroblast growth factor, transforming growth factor-$\beta 2$, platelet derived growth factor, interleukin-1$\alpha$, decorin and collagen types I and III. The periodontal prosthesis is installed as a remedial bioabsorbable device in individuals suffering from periodontal disease after preparing a tooth under treatment in a way familiar to those practiced in the art. This matrix can induce regeneration of periodontal ligaments which hold the tooth to alveolar bone, connective tissues which surround the alveolar bone, and the alveolar bone itself. The foams are recognized by tissue cells because of their composition. The cells receive signals from the foams and are able to attach to them and remodel them. Because of their content of fibroblast growth factor when extracellular matrix particulates are included with them, the foams are angiogenic and capable of attracting a capillary circulation. For each of the prostheses developed, tissue specific, or generic extracellular matrix constituents can be used to provide information required for tissue building and regeneration.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A bioabsorbable composite biopolymer foam comprising a single density biopolymer foam comprising a network of communicating microcompartments having biopolymer molecules and/or biopolymer filaments interspersed within the walls of the microcompartments, wherein the microcompartments have volume dimensions of x, y, and z, wherein x=length, y=width, and z=height, that are substantially equal, and range from about 1 $\mu$m to about 300 $\mu$m, and have an average wall thickness of less than about 10 $\mu$m and a second bioabsorbable biopolymer which is within the single density biopolymer foam.

2. The composite biopolymer foam of claim 1 wherein the biopolymer of the biopolymer foam or the second biopolymer is selected from the group consisting of collagen, alginic acid, polyvinyl alcohol, chondroitin sulfate, laminin, elastin, fibronectin, and fibrinogen.

3. The composite biopolymer foam of claim 2 wherein the biopolymer foam or the second biopolymer is collagen.

4. The composite biopolymer foam of claim 3 wherein the collagen is fetal porcine collagen.

5. The composite biopolymer foam of claim 3 wherein the collagen is polymerized.

6. The composite biopolymer foam of claim 3 wherein the collagen is crosslinked.

7. The composite biopolymer foam of claim 6 wherein the collagen is crosslinked by priming with lysyl oxidase.

8. The composite biopolymer foam of claim 1 further comprising extracellular matrix particulates.

9. The composite biopolymer foam of claim 1 wherein the biopolymer foam and/or the second biopolymer further comprises cells.

10. The composite biopolymer foam of claim 1 wherein the second biopolymer comprises a fiber or fibers.

11. A skin dressing comprising the composite biopolymer foam of claim 10.

12. A skin dressing of claim 11 further comprising extracellular matrix particulates.

13. The skin prosthesis of claim 10 wherein the biopolymer foam is conditioned with human dermal fibroblasts and human keratinocytes such that a stratum corneum is formed.

14. A vascular prosthesis comprising the composite biopolymer foam of claim 10, wherein the composite biopolymer foam is in the form of a tube having an internal surface, an external surface, and a luminal surface.

15. The vascular prosthesis of claim 14, wherein the tube is seeded internally with smooth muscle cells, externally with adventitial fibroblasts, and on its luminal surface with endothelial cells.

16. A periodontal prosthesis comprising the composite biopolymer foam of claim 10, wherein the biopolymer foam is seeded with periodontal ligament cells.

17. The periodontal prosthesis of claim 16, further comprising extracellular matrix particulates.

18. The composite biopolymer foam of claim 1 wherein the second biopolymer comprises a braid.

19. A ligament prosthesis comprising the composite biopolymer foam of claim 10 or 18.

20. The composite biopolymer foam of claim 1 wherein the second biopolymer comprises a fabric.

21. The composite biopolymer foam of claim 20 wherein the fabric is a nonwoven fabric.

22. The composite biopolymer foam of claim 1 wherein the second biopolymer comprises a mesh.

* * * * *